US008643276B2

(12) United States Patent
Maxik et al.

(10) Patent No.: US 8,643,276 B2
(45) Date of Patent: *Feb. 4, 2014

(54) LED LAMP FOR PRODUCING BIOLOGICALLY-CORRECTED LIGHT

(71) Applicant: Biological Illumination, LLC, Satellite Beach, FL (US)

(72) Inventors: Fredric S. Maxik, Indialantic, FL (US); Robert R. Soler, Cocoa Beach, FL (US); David E. Bartine, Cocoa, FL (US)

(73) Assignee: Biological Illumination, LLC, Satellite Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,207

(22) Filed: Oct. 15, 2012

(65) Prior Publication Data
US 2013/0278137 A1     Oct. 24, 2013

Related U.S. Application Data

(63) Continuation of application No. 13/174,339, filed on Jun. 30, 2011, now Pat. No. 8,324,808, which is a continuation-in-part of application No. 12/842,887, filed on Jul. 23, 2010, now Pat. No. 8,253,336.

(51) Int. Cl.
*H01J 7/44* (2006.01)
*F21V 9/00* (2006.01)

(52) U.S. Cl.
USPC ............................................. 315/32; 362/231

(58) Field of Classification Search
USPC ........ 315/32, 294, 297, 307, 309, 224; 362/1, 362/2, 632, 227, 231, 611, 612, 613
See application file for complete search history.

(56) References Cited

U.S. PATENT DOCUMENTS

| 5,046,494 | A | 9/1991 | Searfoss et al. |
| 6,259,572 | B1 | 7/2001 | Meyer, Jr. |
| 6,586,882 | B1 | 7/2003 | Harbers |
| 6,734,639 | B2 | 5/2004 | Chang et al. |

(Continued)

FOREIGN PATENT DOCUMENTS

| EP | 1 888 708 | 2/2008 |
| EP | 2 094 064 A1 | 8/2009 |

(Continued)

OTHER PUBLICATIONS

U.S. Appl. No. 13/559,180, filed Jul. 26, 2012, Maxik et al.

(Continued)

*Primary Examiner* — Minh D A
(74) *Attorney, Agent, or Firm* — Mark R. Malek, Esq.; Daniel C. Pierron; Zies Widerman & Malek

(57) ABSTRACT

A light-emitting diode (LED) lamp for producing a biologically-corrected light. In one embodiment, the LED lamp includes a color filter, which modifies the light produced by the lamp's LED chips, to increase spectral opponency and minimize melatonin suppression. In doing so, the lamp minimizes the biological effects that the lamp may have on a user. The LED lamp is appropriately designed to produce such biologically-correct light while still maintaining commercially acceptable color temperature and color rending properties. Methods of manufacturing such a lamp are provided, as well as equivalent lamps and equivalent methods of manufacture.

15 Claims, 9 Drawing Sheets

(56) References Cited

U.S. PATENT DOCUMENTS

| | | | |
|---|---|---|---|
| 6,762,562 | B2 | 7/2004 | Leong |
| 6,902,296 | B2 | 6/2005 | Searfoss, III |
| 7,095,053 | B2 | 8/2006 | Mazzochette et al. |
| 7,144,131 | B2 | 12/2006 | Rains |
| 7,157,745 | B2 | 1/2007 | Blonder et al. |
| 7,234,844 | B2 | 6/2007 | Bolta et al. |
| 7,252,408 | B2 | 8/2007 | Mazzochete et al. |
| 7,319,293 | B2 | 1/2008 | Maxik |
| 7,497,596 | B2 | 3/2009 | Ge |
| 7,520,607 | B2 | 4/2009 | Casper et al. |
| 7,521,875 | B2 | 4/2009 | Maxik |
| 7,528,421 | B2 | 5/2009 | Mazzochete |
| 7,556,376 | B2 | 7/2009 | Ishak et al. |
| 7,619,372 | B2 | 11/2009 | Garrity |
| 7,633,093 | B2 | 12/2009 | Blonder et al. |
| 7,633,779 | B2 | 12/2009 | Garrity et al. |
| 7,637,643 | B2 | 12/2009 | Maxik |
| 7,708,452 | B2 | 5/2010 | Maxik et al. |
| 7,976,182 | B2 | 7/2011 | Ribarich |
| 8,164,844 | B2 | 4/2012 | Toda et al. |
| 8,253,336 | B2 * | 8/2012 | Maxik et al. ............... 315/32 |
| 8,324,808 | B2 * | 12/2012 | Maxik et al. ............... 315/32 |
| 2003/0030067 | A1 | 2/2003 | Chen |
| 2004/0093045 | A1 | 5/2004 | Bolta |
| 2004/0119086 | A1 | 6/2004 | Yano et al. |
| 2005/0189557 | A1 | 9/2005 | Mazzochette et al. |
| 2005/0267213 | A1 | 12/2005 | Gold et al. |
| 2007/0165193 | A1 | 7/2007 | Kubo et al. |
| 2007/0262714 | A1 | 11/2007 | Bylsma |
| 2008/0119912 | A1 | 5/2008 | Hayes |
| 2008/0231214 | A1 | 9/2008 | Kim et al. |
| 2008/0266690 | A1 | 10/2008 | Toda et al. |
| 2009/0204186 | A1 | 8/2009 | Gruber |
| 2010/0085758 | A1 | 4/2010 | Takahashi et al. |
| 2010/0118510 | A1 | 5/2010 | Bailey et al. |
| 2010/0121420 | A1 | 5/2010 | Fiset et al. |
| 2010/0157573 | A1 | 6/2010 | Toda et al. |
| 2010/0171441 | A1 | 7/2010 | Schlangen et al. |
| 2010/0244735 | A1 | 9/2010 | Buelow |
| 2010/0244740 | A1 | 9/2010 | Alpert et al. |
| 2011/0299277 | A1 | 12/2011 | Ehara |
| 2012/0008326 | A1 | 1/2012 | Jou |
| 2012/0019140 | A1 | 1/2012 | Maxik et al. |

FOREIGN PATENT DOCUMENTS

| | | |
|---|---|---|
| EP | 2 199 657 | 6/2010 |
| EP | 2 242 335 | 10/2010 |
| WO | WO 2009/029575 | 3/2009 |
| WO | WO 2012/012245 A2 | 1/2012 |

OTHER PUBLICATIONS

Charamisinau et al. (2005) "Semiconductor laser insert with Uniform Illumination for Use in Photodynamic Therapy" Appl Opt 44(24):5055-5068.

ERBA Shedding Light on Photosensitivity, One of Epilepsy's Most Complex Conditions. Photosensitivity and Epilepsy. Epilepsy Foundation. Accessed: Aug. 28, 2009. http://www.epilepsyfoundation.org/aboutepilepsy/seizures/photosensitivity-/gerba.cfm.

Figueiro et al. (2004) "Spectral Sensitivity of the Circadian System" Proc. SPIE 5187:207-214.

Figueiro et al. (2008) "Retinal Mechanisms Determine the Subadditive Response to Polychromatic Light by the Human Circadian System" Neurosci Lett 438(2):242-245.

Gabrecht et al. (2007) "Design of a Light Delivery System for the Photodynamic Treatment of the Crohn's Disease" Proc. SPIE 6632:1-9.

Happawana et al. (2009) "Direct De-Ionized Water-Cooled Semiconductor Laser Package for Photodynamic Therapy of Esophageal Carcinoma: Design and Analysis" J Electron Pack 131(2):1-7.

Harding & Harding (1999) "Televised Material and Photosensitive Epilepsy" Epilepsia 40(Suppl. 4):65-69.

Kuller & Laike (1998) "The Impact of Flicker from Fluorescent Lighting on Well-Being, Performance and Physiological Arousal" Ergonomics 41(4):433-447.

Lakatos (2006) "Recent trends in the epidemiology of Inflammatory Bowel Disease: Up or Down?" World J Gastroenterol 12(38):6102-6108.

Ortner & Dorta (2006) "Technology Insight: Photodynamic Therapy for Cholangiocarcinoma" Nat Clin Pract Gastroenterol Hepatol 3(8):459-467.

Rea (2010) "Circadian Light" J Circadian Rhythms 8(1):2.

Rea et al. (2010) "The Potential of Outdoor Lighting for Stimulating the Human Circadian System" Alliance for Solid-State Illumination Systems and Technologies (ASSIST), May 13, 2010, p. 1-11.

Rosco Laboratories Poster "Color Filter Technical Data Sheet: #87 Pale Yellow Green" (2001).

Stevens (1987) "Electronic Power Use and Breast Cancer: A Hypothesis" Am J Epidemiol 125(4):556-561.

Topalkara et al. (1998) "Effects of flash frequency and repetition of intermittent photic stimulation on photoparoxysmal responses" Seizure 7(13):249-253.

Veitch & McColl (1995) "Modulation of Fluorescent Light: Flicker Rate and Light Source Effects on Visual Performance and Visual Comfort" Lighting Research and Technology 27:243-256.

Wang (2005) "The Critical Role of Light in Promoting Intestinal Inflammation and Crohn's Disease" J Immunol 174 (12):8173-8182.

Wilkins et al. (1979) "Neurophysical aspects of pattern-sensitive epilepsy" Brain 102:1-25.

Wilkins et al. (1989) "Fluorescent lighting, headaches, and eyestrain" Lighting Res Technol 21(1):11-18.

* cited by examiner

US 8,643,276 B2

LED LAMP FOR PRODUCING BIOLOGICALLY-CORRECTED LIGHT

CROSS-REFERENCE TO RELATED APPLICATIONS

This application is a continuation of U.S. patent application Ser. No. 13/174,339, which is in turn a continuation-in-part of U.S. patent application Ser. No. 12/842,887, filed on Jul. 23, 2010, which are incorporated herein by reference in their entirety.

FIELD OF THE INVENTION

The present invention relates to light sources; and more specifically to a light-emitting diode (LED) lamp for producing a biologically-corrected light.

BACKGROUND

Melatonin is a hormone secreted at night by the pineal gland. Melatonin regulates sleep patterns and helps to maintain the body's circadian rhythm. The suppression of melatonin contributes to sleep disorders, disturbs the circadian rhythm, and may also contribute to conditions such as hypertension, heart disease, diabetes, and/or cancer. Blue light, and the blue light component of polychromatic light, have been shown to suppress the secretion of melatonin. Moreover, melatonin suppression has been shown to be wavelength dependent, and peak at wavelengths between about 420 nm and about 480 nm. As such, individuals who suffer from sleep disorders or circadian rhythm disruptions continue to aggravate their conditions when using polychromatic light sources that have a blue light (420 nm-480 nm) component.

Curve A of FIG. 1 illustrates the action spectrum for melatonin suppression. As shown by Curve A, a predicted maximum suppression is experienced at wavelengths around about 460 nm. In other words, a light source having a spectral component between about 420 nm and about 480 nm is expected to cause melatonin suppression. FIG. 1 also illustrates the light spectra of conventional light sources. Curve B, for example, shows the light spectrum of an incandescent light source. As evidenced by Curve B, incandescent light sources cause low amounts of melatonin suppression because incandescent light sources lack a predominant blue component. Curve C, illustrating the light spectrum of a fluorescent light source, shows a predominant blue component. As such, fluorescent light sources are predicted to cause more melatonin suppression than incandescent light sources. Curve D, illustrating the light spectrum of a white light-emitting diode (LED) light source, shows a greater amount of blue component light than the fluorescent or incandescent light sources. As such, white LED light sources are predicted to cause more melatonin suppression than fluorescent or incandescent light sources. For additional background on circadian effects of light, reference is made to the following publications, which are incorporated herein by reference in their entirety:

Figueiro, et al., "Spectral Sensitivity of the Circadian System," Lighting Research Center, available at: http://www.lrc.rpi.edu/programs/lightHealth/pdf/spectralSensitivity.pdf.

Rea, et al., "Circadian Light," Journal of Circadian Rhythms, 8:20 (2010).

Stevens, R. G., "Electric power use and breast cancer; a hypothesis," American Journal of Epidemiology, 125:4, pgs. 556-561 (1987).

Veitch, et al., "Modulation of Fluorescent Light: Flicker Rate and Light Source Effects on Visual Performance and Visual Comfort.

As the once ubiquitous incandescent light bulb is replaced by fluorescent light sources (e.g., compact-fluorescent light bulbs) and white LED light sources, more individuals may begin to suffer from sleep disorders, circadian rhythm disorders, and other biological system disruptions. One solution may be to simply filter out all of the blue component (420 nm-480 nm) of a light source. However, such a simplistic approach would create a light source with unacceptable color rendering properties, and would negatively affect a user's photopic response. What is needed is an LED light source with commercially acceptable color rendering properties, which produces minimal melatonin suppression, and thus has a minimal effect on natural sleep patterns and other biological systems.

BRIEF SUMMARY OF THE INVENTION

Provided herein are exemplary embodiments of a light-emitting diode (LED) lamp for producing a biologically-corrected light. In one embodiment, the LED lamp includes a color filter, which modifies the light produced by the lamp's LED chips, to increase spectral opponency and minimize melatonin suppression. In doing so, the lamp minimizes the biological effects that the lamp may have on a user. The LED lamp is appropriately designed to produce such biologically-correct light, while still maintaining a commercially acceptable color temperature and commercially acceptable color rending properties. Methods of manufacturing such a lamp are provided, as well as equivalent lamps and equivalent methods of manufacture.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use an LED lamp in accordance with the present invention. In the drawings, like reference numbers indicate identical or functionally similar elements.

DETAILED DESCRIPTION OF THE FIGURES

The following detailed description of the figures refers to the accompanying drawings that illustrate an exemplary embodiment of an LED lamp for producing a biologically-corrected light. Other embodiments are possible. Modifications may be made to the embodiment described herein without departing from the spirit and scope of the present invention. Therefore, the following detailed description is not meant to be limiting.

Figure 2:
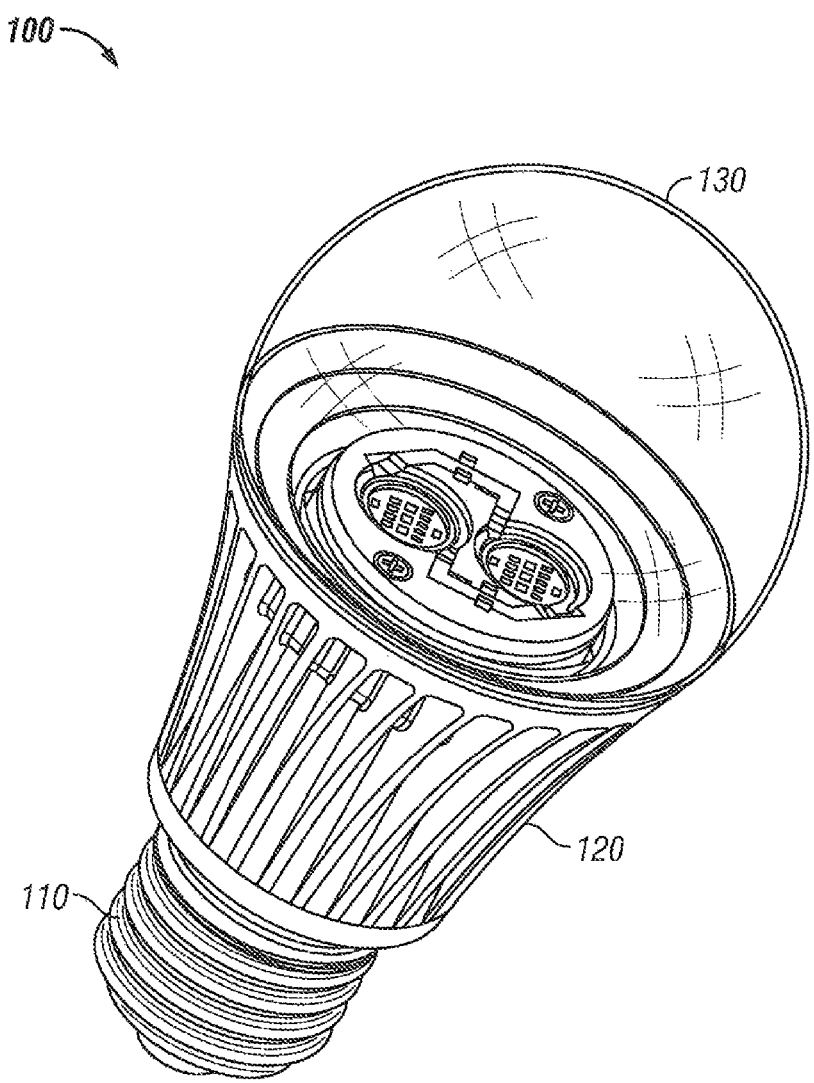
FIG. 2 is a perspective view of an LED lamp in accordance with one embodiment presented herein.

FIG. 2 is a perspective view of an LED lamp (or bulb) 100 in accordance with one embodiment presented herein. As shown in FIG. 2, LED lamp 100 includes a base 110, a heat sink 120, and an optic 130. As will be described below, LED lamp 100 further includes one or more LED chips and dedicated circuitry within LED lamp 100. LED lamp 100 has been designed to produce a biologically-corrected light. The term "biologically-corrected light" is intended to mean "a light that has been modified to minimize or limit biological effects on a user." The term "biological effects" is intended to mean "any impact or change a light source has to a naturally occurring function or process." Biological effects, for example, may include hormone secretion or suppression (e.g., melatonin suppression), changes to cellular function, stimulation or disruption of natural processes, cellular mutations or manipulations, etc.

Base 110 is preferably an Edison-type screw-in shell. Base 110 is preferably formed of an electrically conductive material such as aluminum. In alternative embodiments, base 110 may be formed of other electrically conductive materials such as silver, copper, gold, conductive alloys, etc. Internal electrical leads (not shown) are attached to base 110 to serve as contacts for a standard light socket (not shown).

As known in the art, the durability of an LED chip is usually affected by temperature. As such, heat sink 120, and structures equivalent thereto, serves as means for dissipating heat away from one or more of the LED chips within LED lamp 100. In FIG. 2, heat sink 120 includes fins to increase the surface area of the heat sink. Alternatively, heat sink 120 may be formed of any configuration, size, or shape, with the general intention of drawings heat away from the LED chips within LED lamp 100. Heat sink 120 is preferably formed of a thermally conductive material such as aluminum, copper, steel, etc.

Optic 130 is provided to surround the LED chips within LED lamp 100. As used herein, the terms "surround" or "surrounding" are intended to mean partially or fully encapsulating. In other words, optic 130 surrounds the LED chips by partially or fully covering one or more LED chips such that light produced by one or more LED chips is transmitted through optic 130. In the embodiment shown, optic 130 takes a globular shape. Optic 130, however, may be formed of alternative forms, shapes, or sizes. In one embodiment, optic 130 serves as an optic diffusing element by incorporating diffusing technology, such as described in U.S. Pat. No. 7,319,293 (which is incorporated herein by reference in its entirety). In such an embodiment, optic 130, and structures equivalent thereto, serves as a means for defusing light from the LED chips. In alternative embodiments, optic 130 may be formed of a light diffusive plastic, may include a light diffusive coating, or may having diffusive particles attached or embedded therein.

In one embodiment, optic 130 includes a color filter applied thereto. The color filter may be on the interior or exterior surface of optic 130. The color filter is used to modify the light output from one or more of the LED chips. The color filter modifies the light so as to increase spectral opponency, and thereby minimize the biological effects of the light, while maintaining commercially acceptable color rendering characteristics. It is noted that a color filter in accordance with the present invention is designed to do more than simply filter out the blue component light from the LED chips. Instead the color filter is configured to take advantage of spectral opponency; namely the phenomenon wherein wavelengths from one portion of the spectrum excite a response, while wavelengths from another portion inhibit a response.

For example, recent studies have shown that spectral opponency results in certain wavelengths of light negating the melatonin suppression caused by blue light. As such, the inventors have discovered that by designing a color filter that filters some (i.e., not all) of the blue component of the LED chips, while increasing the yellow component (yellow being the spectral opponent to blue), an LED lamp can be designed to maintain commercially acceptable color rendering properties, while minimizing the biological effects of the LED lamp. By minimizing the biological effects (e.g., reducing melatonin suppression), the LED lamp can provide relief for people who suffer from sleep disorders, circadian rhythm disruptions, and other biological system disruptions.

Figure 3:
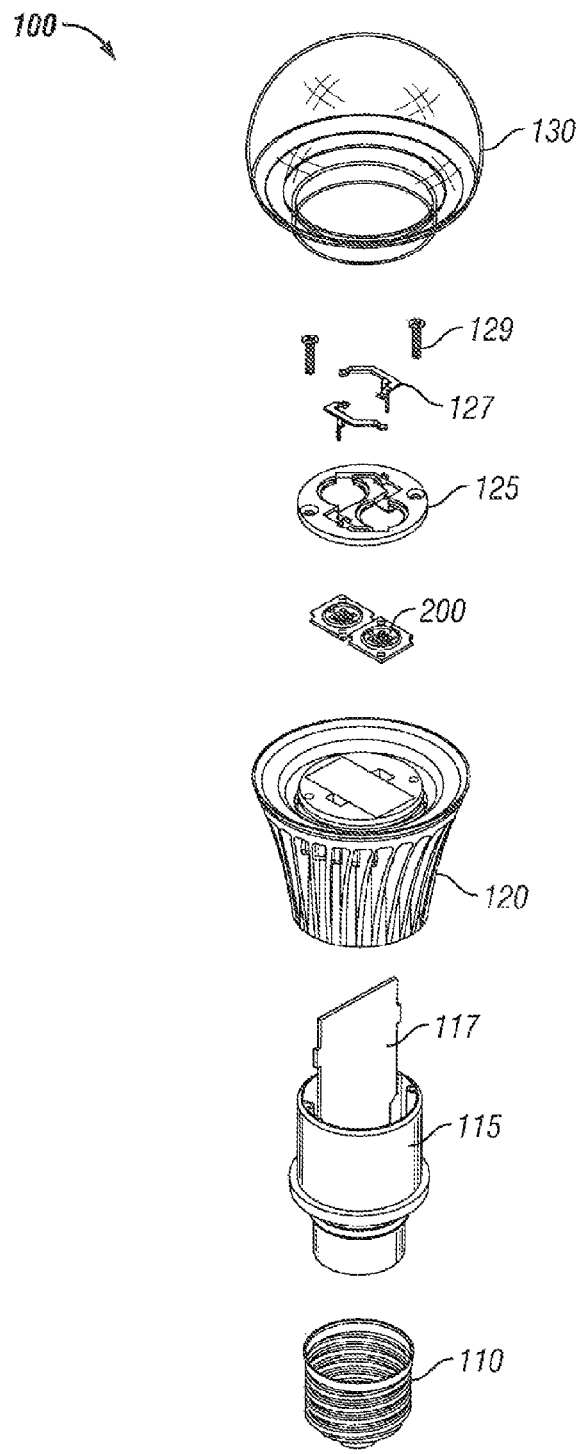
FIG. 3 is an exploded view of the LED lamp of FIG. 2.

FIG. 3 is an exploded view of LED lamp 100, illustrating internal components of the lamp. As shown, in addition to the components described above, LED lamp 100 also includes at least a housing 115, a printed circuit board (PCB) 117, one or more LED chips 200, a holder 125, spring wire connectors 127, and screws 129.

PCB 117 includes dedicated circuitry to power, drive, and control one or more LED chips 200. PCB 117 includes at least a driver circuit and a power circuit. The circuitry on PCB 117 serves as a means for driving the LED chips 200. In one embodiment the driver circuit is configured to drive LED chips 200 with a ripple current at frequencies greater than 200 Hz. A ripple current at frequencies above 200 Hz is chosen to avoid biological effects that may be caused by ripple currents at frequencies below 200 Hz. For example, studies have shown that some individuals are sensitive to light flicker below 200 Hz, and in some instances experience aggravated headaches, seizures, etc.

As used herein, the term "LED chips" is meant to broadly encompass LED dies, with or without packaging and reflectors, that may or may not be treated (e.g., with applied phosphors). In the embodiment shown, however, LED chips 200 are "white LED chips" having a plurality of blue-pumped (about 465 nm) LED dies with a phosphor applied thereto. In another embodiment, LED chips 200 are white LED chips having a plurality of blue-pumped (about 450 nm) LED dies with a phosphor applied thereto. In alternative embodiments, LED chips 200 employ a garnet based phosphor, such as a Yttrium aluminum garnet (YAG) or dual-YAG phosphors, orthosilicate based phosphors, or quantum dots to create white light. In one embodiment, LED chips 200 emit light having a color temperature between about 2500K and about 2900K, and more preferably about 2700K.

Figure 4:
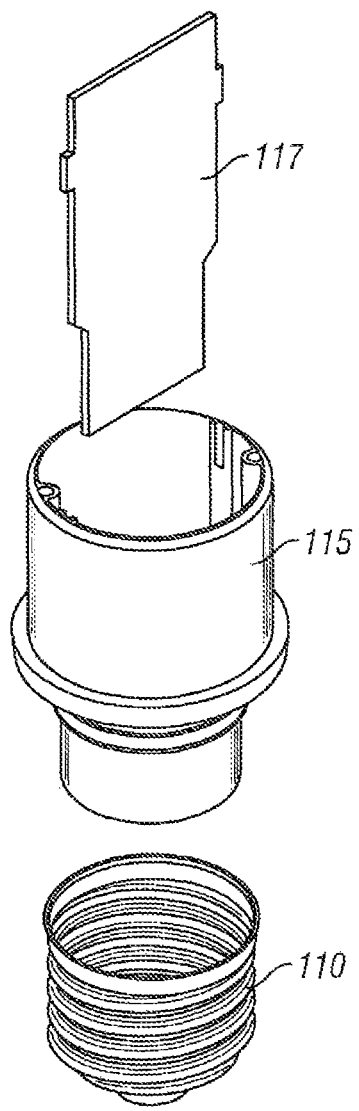
FIG. 4 is an exploded view of a portion of the LED lamp of FIG. 2.

FIGS. 4-7 are exploded views of portions of LED lamp 100. FIGS. 4-7 illustrate how to assemble LED lamp 100. As shown in FIG. 4, base 110 is glued or crimped onto housing 115. PCB 117 is mounted within housing 115. Insulation and/or potting compound (not shown) may be used to secure PCB 117 within housing 115. Electrical leads (not shown) on PCB 117 are coupled to base 110 to form the electrical input leads of LED lamp 100.

Figure 5:
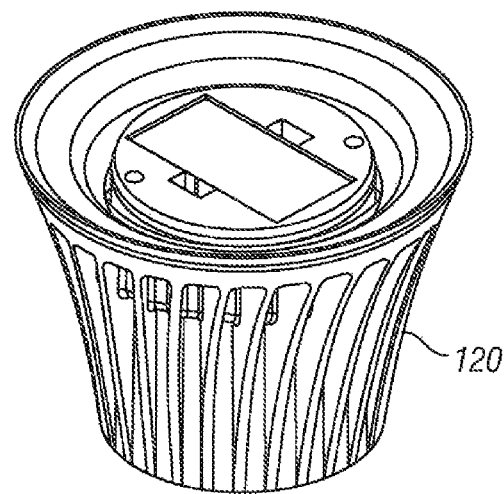
FIG. 5 is an exploded view of a portion of the LED lamp of FIG. 2.
Figure 5:
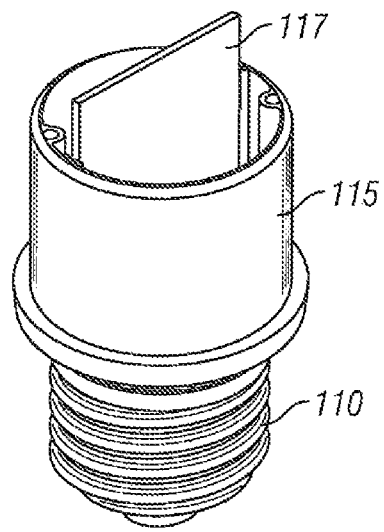
Figure 6:
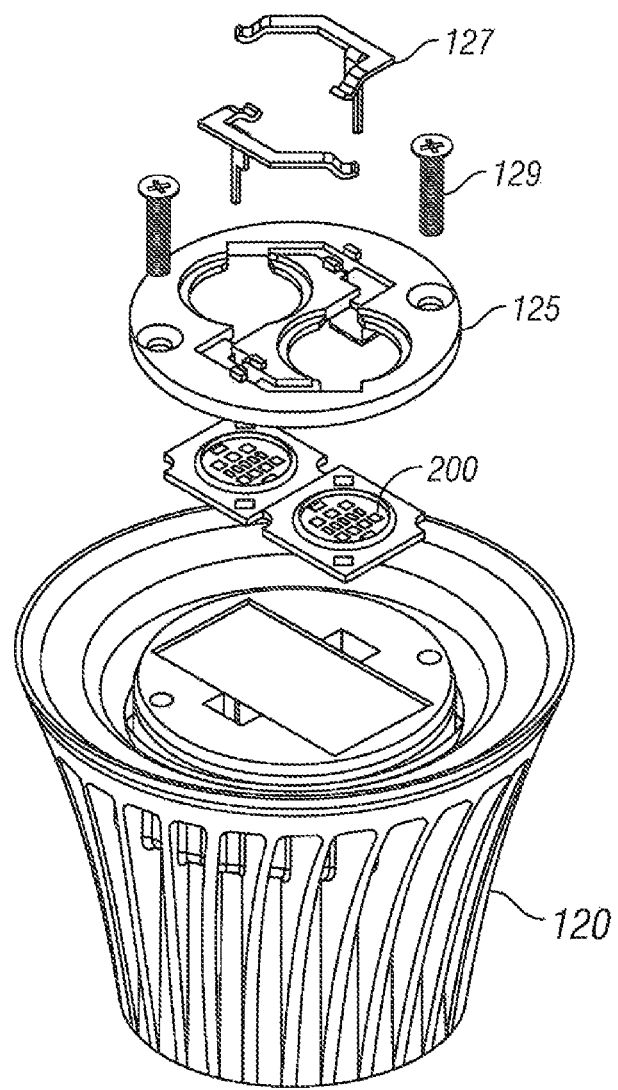
FIG. 6 is an exploded view of a portion of the LED lamp of FIG. 2.
Figure 7:
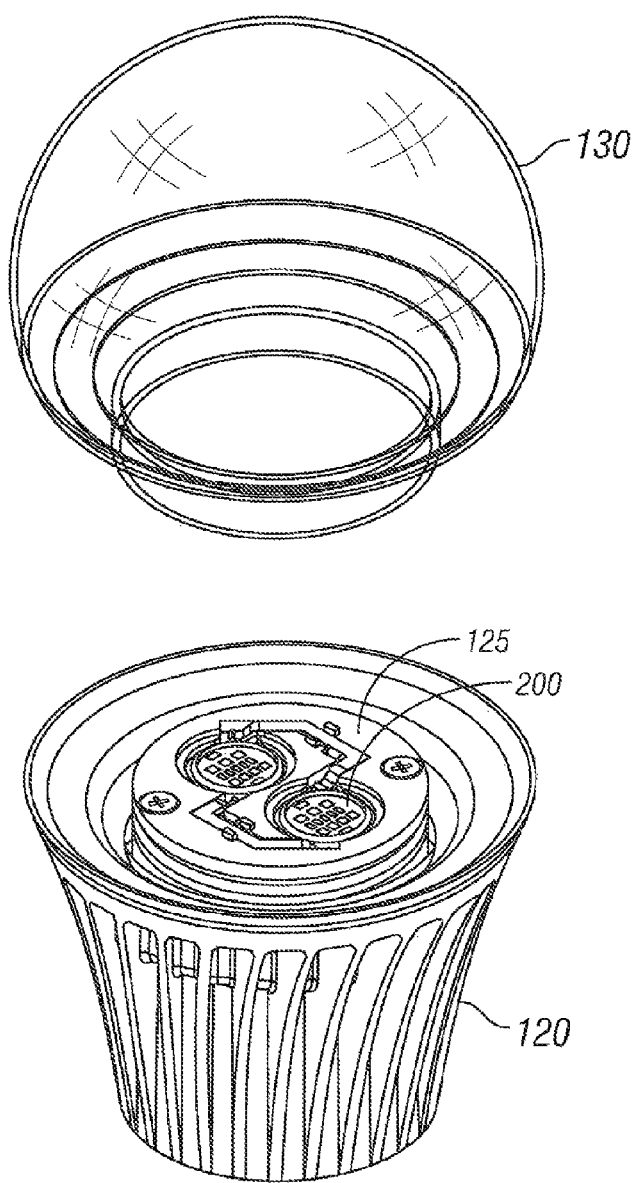
FIG. 7 is an exploded view of a portion of the LED lamp of FIG. 2.

As shown in FIG. 5, heat sink 120 is disposed about housing 115. As shown in FIG. 6, two LED chips 200 are mounted onto heat sink 120, and maintained in place by holder 125. While two LED chips 200 are shown, alternative embodiments may include any number of LED chips (i.e., one or more). Screws 129 are used to secure holder 125 to heat sink 120. Screws 129 may be any screws known in the art (e.g., M2 plastite screws). Spring wire connectors 127 are used to connect LED chips 200 to the driver circuit on PCB 117. In an alternative embodiment, LED chips 200 (with or without packaging) may be attached directly to heat sink 120 without the use of holder 125, screws 129, or connectors 127. As shown in FIG. 7, optic 130 is then mounted on and attached to heat sink 120.

Figure 8:
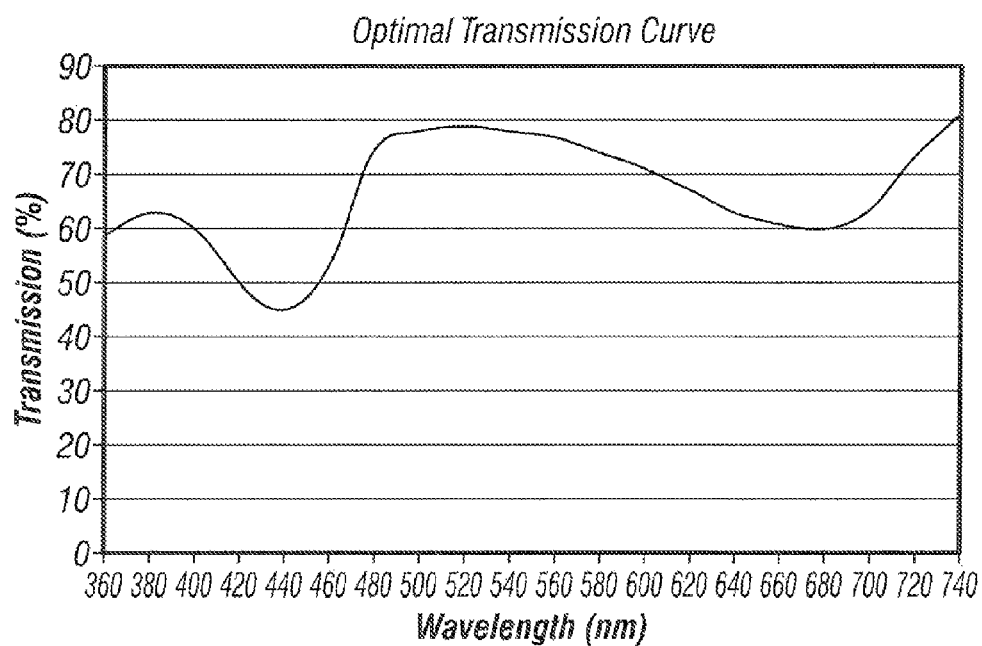
FIG. 8 illustrates an optimal transmission curve for a color filter in accordance with one embodiment presented herein.

FIG. 8 illustrates an optimal transmission curve for a color filter in accordance with one embodiment of the present invention. The inventors have found that the transmission curve of FIG. 8 provides increased spectral opponency, which minimizes biological effects, while maintaining a commercially acceptable color rendering index. For example, application of a color filter having the transmission curve of FIG. 8 to LED lamp 100 results in a lamp having a color rendering index above 70, and more preferably above 80, and a color temperature between about 2,700K and about 3,500K, and more preferably about 3,015K. In one embodiment, LED lamp 100 produces no UV light. In one embodiment, LED lamp 100 produces 400-800 lumens.

In one embodiment, the color filter is a ROSCOLUX #87 Pale Yellow Green color filter. In an alternative embodiment, the color filter has a total transmission of about 85%, a thickness of about 38 microns, and is formed of a deep-dyed polyester film.

In yet another embodiment, the color filter has transmission percentages within +/−10%, at one or more wavelengths, in accordance with the following table:

| Wavelength | Transmission (%) |
|---|---|
| 360 | 59 |
| 380 | 63 |
| 400 | 60 |
| 420 | 50 |
| 440 | 45 |
| 460 | 53 |
| 480 | 75 |
| 500 | 78 |
| 520 | 79 |
| 540 | 78 |
| 560 | 77 |
| 580 | 74 |
| 600 | 71 |
| 620 | 67 |
| 640 | 63 |
| 660 | 61 |
| 680 | 60 |
| 700 | 64 |
| 720 | 74 |
| 740 | 81 |

Figure 10:
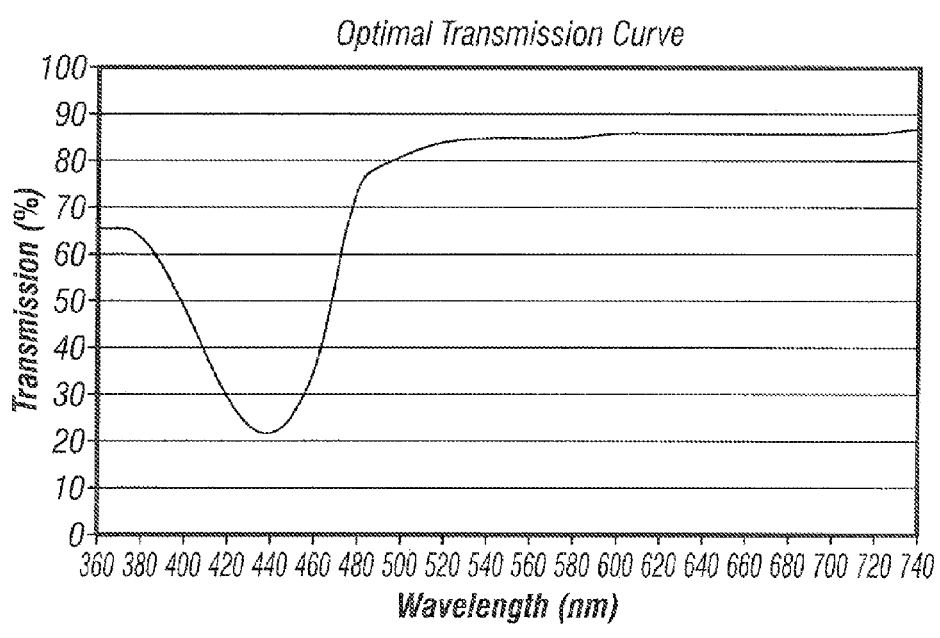
FIG. 10 illustrates an optimal transmission curve for a color filter in accordance with one embodiment presented herein.

FIG. 10 illustrates an optimal transmission curve for a color filter in accordance with one embodiment of the present invention. The inventors have found that the transmission curve of FIG. 10 provides increased spectral opponency, which minimizes biological effects, while maintaining a commercially acceptable color rendering index.

In one embodiment, the color filter is a ROSCOLUX #4530 CALCOLOR 30 YELLOW color filter. In an alternative embodiment, the color filter has a total transmission of about 75%, a thickness of about 50 microns, and is formed of a deep-dyed polyester film.

In yet another embodiment, the color filter has transmission percentages within +/−10%, at one or more wavelengths, in accordance with the following table:

| Wavelength | Transmission (%) |
|---|---|
| 360 | 66 |
| 380 | 64 |
| 400 | 49 |
| 420 | 30 |
| 440 | 22 |
| 460 | 35 |
| 480 | 74 |
| 500 | 81 |
| 520 | 84 |
| 540 | 85 |
| 560 | 85 |
| 580 | 85 |
| 600 | 86 |
| 620 | 86 |
| 640 | 86 |
| 660 | 86 |
| 680 | 86 |
| 700 | 86 |
| 720 | 86 |
| 740 | 87 |

In still another embodiment, there is provided a biologically-corrected LED lamp, having a plurality of blue-pump LED chips. The LED chips may have a peak emission of about 450 nm. The lamp further includes a color filter configured to attenuate the 450 nm emission and provide a polychromatic output with peak emissions at: about 475 nm with an about 25 nm half-peak width; about 500 nm with an about 30 nm half-peak width; and/or a peak between about 590 nm and about 625 nm with an about 20 nm half-peak width.

As used herein, the "means for increasing the spectral opponency of the light output to limit the biological effect of the light output" should include the herein described embodiments of color filters, and equivalents thereto. For example, color filters with equivalent transmission characteristics may be formed of absorptive or reflective coatings, thin-films, body-colored polycarbonate films, deep-dyed polyester films, surface-coated films, etc. In an alternative embodiment, pigment may be infused directly into the optic in order to produce the transmission filter effects. In another alternative embodiment, phosphors and/or quantum dots may be employed as "means for increasing the spectral opponency of the light output to limit the biological effect of the light output." For example, a combination of green converted and red converted phosphors can applied to the blue LED pump to create the light spectrum depicted in Curve E of FIG. 9 (discussed below).

Color filters having the transmission curve shown in, for example, FIGS. 8 and 10, and equivalents thereto, also minimizes the circadian-to-photopic ratio. As such, the color filters described herein, and equivalents thereto, serve as a means for minimizing the circadian-to-photopic ratio of a lamp. The term "a circadian-to-photopic ratio" is defined as "the ratio of melatonin suppressive light to total light output." More specifically, the circadian-to-photopic ratio may be calculated as a unit-less ratio defined as:

$$\frac{\rho}{\phi} \text{ where}$$

$$\rho = K_1 \int_{380}^{780} P_\lambda C(\lambda) \delta\lambda$$

and where $$\phi = K_2 \int_{380}^{780} P_\lambda V(\lambda) \delta\lambda$$

In one embodiment, $K_1$ is set to equal $K_2$. $P_\lambda$ is the spectral power distribution of the light source. $C(\lambda)$ is the circadian function (presented in the above referenced Figueiro et al. and Rea et al. publications). $V(\lambda)$ is the photopic luminous efficiency function (presented in the above referenced Figueiro et al. and Rea et al. publications). In one embodiment, the LED lamp produced in accordance with the present invention has a circadian-to-photopic ratio below about 0.10, and more preferably a circadian-to-photopic ratio below about 0.05, and most preferably a zero circadian-to-photopic ratio (i.e., no melatonin suppressive light is produced, although the lamp is generating a measurable amount of total light output). By way of contrast, the inventors have found the circadian-to-photopic ratio of a 2856K incandescent source to be about 0.138; of a white LED to be about 0.386; and of a fluorescent light source to be about 0.556.

Figure 1:
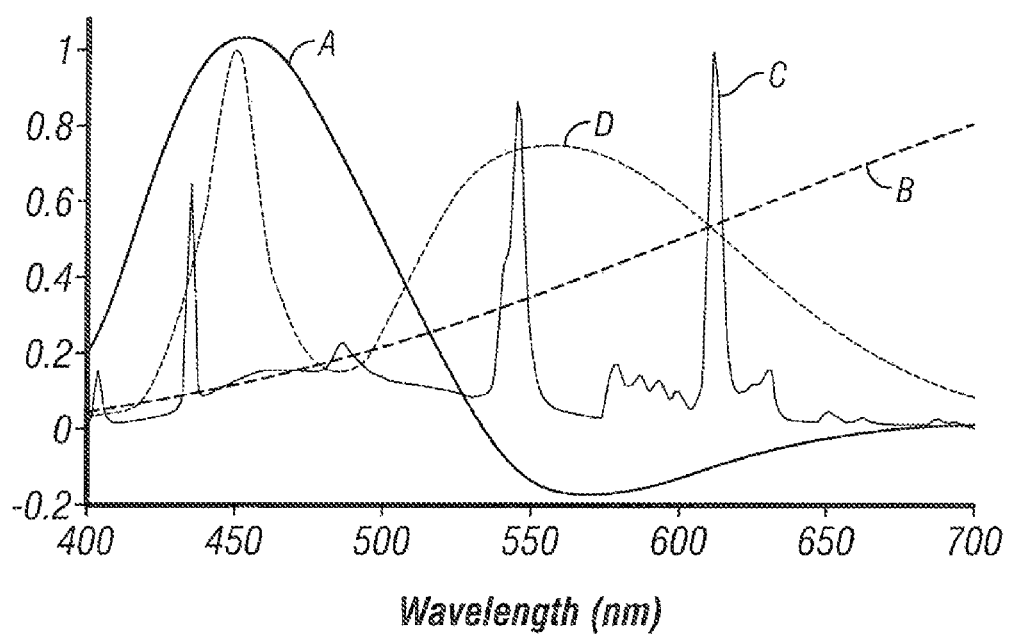
FIG. 1 illustrates the light spectra of conventional light sources in comparison to a predicted melatonin suppression action spectrum for polychromatic light.
Figure 9:
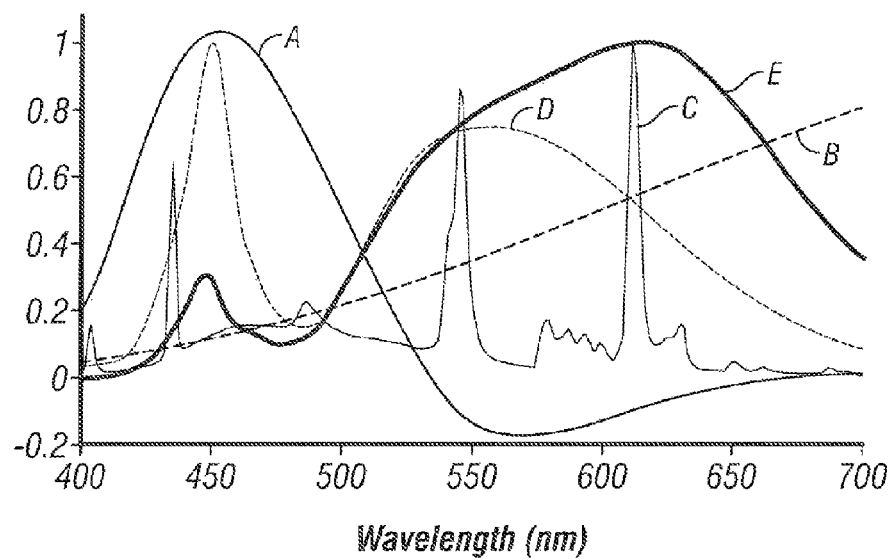
FIG. 9 illustrates the light spectra of conventional light sources in comparison to the predicted melatonin suppression action spectrum for polychromatic light, as illustrated in FIG. 1, and further including the light spectrum of an LED lamp in accordance with one embodiment presented herein.

FIG. 9 illustrates the light spectra of conventional light sources in comparison to the predicted melatonin suppression action spectrum, as illustrated in FIG. 1, and further including the light spectrum of an LED lamp in accordance with one embodiment of the present invention (Curve E). As shown by Curve E, a color filter in accordance with the present invention does not necessarily filter out the entire blue component light of the LED chips. In fact, Curve E shows a blue component spike at about 450 nm. However, the color filter minimizes the biological effects of the light by compensating with spectral opponency. In other words, the color filter is designed to increase the yellow component light, which is the spectral opponent of blue light. As such, the resulting light source can maintain commercially acceptable color rendering properties, while minimizing biological effects.

EXAMPLES

The following paragraphs serve as example embodiments of the above-described systems. The examples provided are prophetic examples, unless explicitly stated otherwise.

Example 1

In one example, there is provided a biologically-corrected LED lamp, comprising a housing; a driver circuit disposed within the housing; a plurality of LED chips electrically coupled to and driven by the driver circuit, wherein the plurality of LED chips produce a light output; and an optic element surrounding the plurality of LED chips. The optic element has a color filter applied thereto. The color filter is configured to increase spectral opponency to thereby decrease a melatonin suppressive effect of the light output of the plurality of LED chips. The color filter may have a total transmission of about 75%, a thickness of about 50 microns, and is formed of a deep-dyed polyester film.

In one embodiment, the lamp further comprises a heat sink disposed about the housing.

In one embodiment, the plurality of LED chips are blue-pumped white LED chips. In an embodiment, light output of the plurality of LED chips has a color temperature between about 2,500K and about 2,900K. In another embodiment, the light output of the plurality of LED chips has a color temperature of about 2,700K.

In one embodiment, the lamp has a color rendering index above 70, and a color temperature between about 2,700K and about 3,500K.

Example 2

In another example, there is provided a biologically-corrected LED lamp, comprising a housing; a driver circuit disposed within the housing; a plurality of LED chips electrically coupled to and driven by the driver circuit, wherein the plurality of LED chips produce a light output; and an optic element surrounding the plurality of LED chips. The optic element has a color filter applied thereto. The color filter is configured to increase spectral opponency to thereby decrease a melatonin suppressive effect of the light output of the plurality of LED chips. The color filter is a ROSCOLUX #4530 CALCOLOR 30 YELLOW color filter.

Example 3

In an example, there is provided a biologically-corrected LED lamp, having a color rendering index above 70 and a color temperature between about 2,700K and about 3,500K, wherein the lamp produces a spectral power distribution that increases spectral opponency to thereby minimize melatonin suppression. The lamp comprises: a base; a housing attached to the base; a power circuit disposed within the housing and having electrical leads attached to the base; a driver circuit disposed within the housing and electrically coupled to the power circuit; a heat sink disposed about the housing; a plurality of LED chips electrically coupled to and driven by the driver circuit, wherein the plurality of LED chips are coupled to the heat sink, wherein the plurality of LED chips are blue-pumped white LED chips that produce light having a color temperature of about 2,700K, and wherein the driver circuit is configured to drive the plurality of LED chips with a ripple current at frequencies greater than 200 Hz; and optic diffusing element mounted on the heat sink and surrounding the plurality of LED chips, wherein the optic diffusing element has a color filter applied thereto, and wherein the color filter is configured to increase spectral opponency to thereby decrease a melatonin suppressive effect of a light output from the plurality of LED chips. The color filter has a transmission of about 22% at a wavelength of about 440 nm, a transmission of about 35% at a wavelength of about 460 nm, a transmission of about 74% at a wavelength of about 480 nm, a transmission of about 85% at a wavelength of about 560 nm, a transmission of about 85% at a wavelength of about 580 nm, and a transmission of about 86% at a wavelength of about 600 nm.

Example 4

In another example, there is provided a method of minimizing a biological effect produced by a white LED lamp, wherein the LED lamp includes a housing, a driver circuit disposed within the housing, a plurality of LED chips electrically coupled to and driven by the driver circuit, wherein the plurality of LED chips produce a light output, and an optic element surrounding the plurality of LED chips. The method comprises applying to the optic element a color filter having a transmission of about 22% at a wavelength of about 440 nm, a transmission of about 35% at a wavelength of about 460 nm, a transmission of about 74% at a wavelength of about 480 nm, a transmission of about 85% at a wavelength of about 560 nm, a transmission of about 85% at a wavelength of about 580 nm, and a transmission of about 86% at a wavelength of about 600 nm. The method may also comprise configuring the driver circuit to drive the LED chip with a ripple current at frequencies greater than 200 Hz.

Example 5

In yet another example, there is provided a method of increasing spectral opponency of an LED lamp comprising: applying to the LED lamp a ROSCOLUX #4530 CAL-COLOR 30 YELLOW color filter.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A biologically-corrected light-emitting diode (LED) lamp, comprising:
a housing;
a driver circuit disposed within the housing;
a plurality of LED chips electrically coupled to and driven by the driver circuit, wherein the plurality of LED chips produce a light output; and
an optic element operable to receive light from the plurality of LED chips, wherein the optic element has a color filter applied thereto, wherein the color filter is configured to increase spectral opponency to thereby decrease a biological effect of the light output of the plurality of LED chips, and wherein the color filter has a total transmission of about 75%.

2. A biologically-corrected lamp according to claim 1 wherein the color filter is configured to attenuate the 450 nanometers emission and provide a polychromatic output with peak emissions at least one of about 475 nanometers with an about 25 nanometers half-peak width, about 500 nanometers with an about 30 nanometers half-peak width, and between about 590 nanometers and about 625 nanometers with an about 20 nanometers half-peak width.

3. A biologically-corrected LED lamp according to claim 1 wherein the lamp produces approximately no ultraviolet light.

4. A biologically-corrected LED lamp according to claim 1 wherein the lamp has a color rendering index above about 80.

5. A biologically-corrected LED lamp according to claim 1, wherein the lamp has a color temperature within the range from about 2,500 Kelvin to about 3,500 Kelvin.

6. A biologically-corrected light-emitting diode (LED) lamp having a color rendering index above 80 and a color temperature between within the range from about 2,500 Kelvin to about 3,500 Kelvin wherein the lamp produces a spectral power distribution that increases spectral opponency to thereby minimize melatonin suppression, the lamp comprising:
a base;
a housing attached to the base;
a power circuit disposed within the housing and having electrical leads attached to the base;
a driver circuit disposed within the housing and electrically coupled to the power circuit;
a heat sink disposed about the housing;
a plurality of LED chips electrically coupled to and driven by the driver circuit; and
an optic diffusing element mounted on the heat sink and surrounding the plurality of LED chips;
wherein the plurality of LED chips are thermally coupled to the heat sink;
wherein the plurality of LED chips are blue-pumped white LED chips that produce light having a color temperature of between about 2,700 Kelvin and 3500 Kelvin;
wherein the driver circuit is configured to drive the plurality of LED chips with a ripple current at frequencies greater than about 200 Hz;
wherein the optic diffusing element has a color filter applied thereto;
wherein the color filter is configured to increase spectral opponency to thereby decrease a melatonin suppressive effect of a light output from the plurality of LED chips; and
wherein the color filter has a total transmission of between about 65% and 85%.

7. A biologically-corrected LED lamp according to claim 6 wherein the color temperature is greater than 3500K.

8. A biologically-corrected LED lamp according to claim 6 wherein the color filter has a transmission of between about 12% and 32% at a wavelength of about 440 nanometers, a transmission of between about 25% and 45% at a wavelength of about 460 nanometers, a transmission of between about 64% and 84% at a wavelength of about 480 nanometers, a transmission of between about 75% and 100% at a wavelength of about 560 nanometers, a transmission of between about 75% and 100% at a wavelength of about 580 nanometers, and a transmission of between about 76% and 100% at a wavelength of about 600 nanometers.

9. A biologically-corrected LED lamp according to claim 6 wherein the color filter comprises a surface-coated film on a portion of the optic diffusing element.

10. A biologically-corrected LED lamp according to claim 6 wherein the color filter comprises one or more of phosphors and quantum dots.

11. A biologically-corrected LED lamp according to claim 9 wherein the one or more phosphors or quantum dots are infused directly into the optic.

12. A biologically-corrected LED lamp according to claim 10 wherein the infused optic comprises a polycarbonate.

13. A biologically-corrected LED lamp according to claim 6 wherein a combination of green converted phosphors and red converted phosphors are applied to the blue LED pump.

14. A method of minimizing a biological effect produced by a white light-emitting diode (LED) lamp, wherein the LED lamp includes a housing, a driver circuit disposed within the housing, a plurality of LED chips electrically coupled to and driven by the driver circuit, wherein the plurality of LED chips produce a light output, and an optic element surrounding the plurality of LED chips, the method comprising the step of applying to the optic element a color filter having a transmission of between about 12% and 32% at a wavelength of about 440 nanometers, a transmission of between about 25% and 45% at a wavelength of about 460 nanometers, a transmission of between about 64% and 84% at a wavelength of about 480 nanometers, a transmission of between about 75% and 100% at a wavelength of about 560 nanometers, a transmission of between about 75% and 100% at a wavelength of about 580 nanometers, and a transmission of between about 76% and 100% at a wavelength of about 600 nanometers.

15. A method according to claim 14 further comprising the step of configuring the driver circuit to drive the LED chip with a ripple current at frequencies greater than 200 Hz.

* * * * *